United States Patent [19]

McConaghy, Jr. et al.

[11] 4,083,874

[45] Apr. 11, 1978

[54] PROCESS FOR PRODUCTION OF ALLYLAMINES FROM PI-ALLYL PALLADIUM COMPLEXES

[75] Inventors: J. S. McConaghy, Jr., University City; F. E. Paulik, St. Louis County, both of Mo.

[73] Assignee: Monsanto Company, St. Louis, Mo.

[21] Appl. No.: 705,320

[22] Filed: Jul. 14, 1976

[51] Int. Cl.² ............................................... C07C 85/22
[52] U.S. Cl. .......................... 260/585 R; 260/293.52; 260/570.7; 260/570.8 R; 260/574; 260/577; 260/583 H; 544/98
[58] Field of Search .......... 260/583 H, 585 R, 585 A, 260/581, 577, 654 R

[56] References Cited

U.S. PATENT DOCUMENTS

| 3,584,020 | 6/1971 | Bach | 252/431 C X |
|---|---|---|---|
| 3,642,902 | 2/1972 | Bach et al. | 260/585 R |
| 3,719,701 | 3/1973 | Bach | 260/465.9 |
| 3,855,321 | 12/1974 | Bach et al. | 260/654 R |

OTHER PUBLICATIONS

Akermark et al., "Tetrahedron Letters", No. 43, pp. 3733–3736, (1975).
Kuran et al., "Journal of Organometallic Chemistry", vol. 40, pp. 647–648, (1972).

*Primary Examiner*—Daniel E. Wyman
*Assistant Examiner*—John J. Doll
*Attorney, Agent, or Firm*—J. C. Logomasini; P. L. Passley; N. E. Willis

[57] ABSTRACT

The present invention provides a process for the production of allylic amines which comprises reacting a pi-allyl palladium complex with ammonia or an amine having a reactive hydrogen attached to the nitrogen atom and a cupric salt, the reaction taking place at a temperature below the decomposition temperature of the complex and in solution in a solvent for the pi-allyl palladium complex.

12 Claims, No Drawings

PROCESS FOR PRODUCTION OF ALLYLAMINES FROM PI-ALLYL PALLADIUM COMPLEXES

BACKGROUND OF THE INVENTION

This invention relates to a process for the production of unsaturated amines and specifically to a process for producing such amines from the reaction of ammonia or an amine with a pi-allyl palladium complex.

The use of unsaturated amines as intermediates in the production of a wide range of agriculture chemicals, herbicides and plastics is well-known and a prime object of the present invention is to provide a means of obtaining such amines in good yields.

The production of allylamines from pi-allyl palladium complexes is fully described in U.S. Pat. No. 3,642,902 which claims:

"A liquid phase process for preparing allylic amines which comprises reacting a pi-allyl palladium complex with ammonia or an amine having a reactive hydrogen atom attached to the amine nitrogen atom at a temperature below the decomposition temperature of said complex, said process being conducted in a liquid selected from the group consisting of said amine and a solvent of the formula

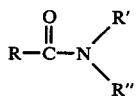

wherein R, R' and R" are selected from the group consisting of hydrogen, alkyl and phenyl with the proviso that where either R or R' is linked to R" then R and R" or R' and R", respectively, form an alkylene radical, and wherein the sum of carbon atoms in R, R' and R" is less than 12."

The theory of the reaction and the structure of the pi-allyl complexes is fully set forth in the above indicated patent and a method by which such complexes may be formed is described in U.S. Pat. No. 3,584,020.

It has now been found possible to improve greatly the effectiveness of the reaction described in U.S. Pat. No. 3,642,902 and the present application sets forth ways in which such improvement can be obtained.

DESCRIPTION OF THE INVENTION

The present invention provides a process for the production of allylic amines which comprises reacting a pi-allyl palladium complex with ammonia or an amine having a reaction hydrogen attached to the nitrogen atom and a cupric salt, the reaction taking place at a temperature below the decomposition temperature of the complex and in solution in a solvent for the pi-allyl palladium complex.

The reaction that takes place in the process of the invention is somewhat different to that described in U.S. Pat. No. 3,642,902 in which a typical reaction would be:

In the process described herein however a typical reaction is as follows:

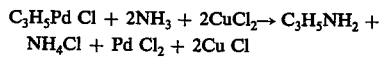

It can be seen therefore that the cupric salt acts as an oxidizing agent and leaves the palladium in the form of a palladium salt that can be converted by known means to an allyl palladium complex.

This reaction is significantly different in that it proceeds at a much faster rate and it is possible to take it to a greater degree of completion. It should also be noted that the allylamine can itself react with the complex to form di- and tri-allylamines and these will be present in the product obtained.

The nitrogen containing compounds employed in the preparation of allyl amines according to this invention are those having at least one active hydrogen atom attached to a nitrogen atom. These include ammonia, primary and secondary amines which may be represented by the following structural formula:

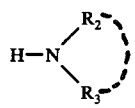

wherein $R_2$ and $R_3$ may be hydrogen, any aliphatic, alicyclic or aromatic radical or where $R_2$ and $R_3$ may represent a divalent radical which forms a nitrogen containing heterocycle as indicated by the dotted line. Among such radicals are various straight and branched chain alkyl radicals, cycloalkyl radicals and aromatic carbocyclic and heterocyclic radicals which may include any substituent which is unreactive with the pi-allyl palladium complex. Such unreactive substituents include ether groups, ketone groups, nitro groups and the like. Exemplary of the amines which may be employed in the process of this invention are ammonia, ethylamine, n-propylamine, aniline, N-methyl aniline, diethylamine, dibutylamine, methylethyl amine, mono- and di-allylamine, cyclohexylamine, morpholine and piperidine.

Allyl amines are prepared according to this invention by contacting the pi-allyl palladium complex, the cupric salt and ammonia, a primary or secondary amine in solution in a suitable solvent and at a temperature below the decomposition, temperature of the pi-allyl palladium complex and, preferably, at a temperature ranging from about 50° C. to about 175° C. It is desirable to stir the reaction mixture during the course of the reaction to ensure adequate contact between the reactants in solution. The progress of the reaction may conveniently be followed by a vapor phase chromatographic analysis to the point of completion. The reaction medium must be one which completely or partially dissolves the allyl palladium complex. Although the pi-allyl palladium complex may be prepared separately and thereafter dissolved in the solvent and reacted with the cupric salt and the ammonia or appropriate amine it has been found most convenient to add the cupric salt and the ammonia or amine to the reaction mixture in which the pi-allyl palladium complex was formed in an amount sufficient to ensure complete reaction of the more expensive pi-allyl palladium complex. While neither the order of addition of the reactants nor the amount of either reactant (apart from the use of a stoichiometric excess of ammonia) has been found to be critical, the process is most desirably conducted by adding an excess of ammonia or the amine beyond that needed to co-ordinate the cupric salt.

Upon completion of the reaction the allyl amine product and any excess amine may be separated from the reaction mixture by fractionation.

The cupric salt can be for example a halide such as cupric bromide or cupric chloride, the acetate, sulfate or nitrate. The prefered salts are however cupric chloride and cupric bromide.

The ammonia or amine is added to the reaction mixture in a stoichiometric excess since it also serves to complex the cupric salt. Preferably therefore the amount added is also in excess of the amount necessary to carry out this function.

In theory it is possible to use any salt that is capable of oxidizing the palladium to the +2 state but it has been found that the cupric salts combine ready availability and high activity that makes them particularly adapted to the process herein described. After use the cuprous salt by-product may be easily re-oxidized to the +2 state using air, to provide a fresh supply of cupric salt for the reaction.

The allyl palladium complex may be represented by the formula $C_3H_5PdX$ wherein X is an anionic radical. Most commonly this is an inorganic anion such as chloride, bromide or sulfate though others such as acetate could be used. In practice it is usual to provide that the anionic radical should be the same in both the pi-allyl palladium complex and the cupric salt. Thus the preferred anions are chloride and bromide.

The effectiveness of the reaction can be greatly enhanced by the presence of a ligand material capable of stabilizing palladium in solution. Suitable ligands include compounds having the formula $R'_3M$ where M is phosphorus, bismuth, antimony or arsenic and the three R' groups may be the same or different hydrocarbyl or hydrocarbyloxy groups such as phenyl, tolyl, phenoxy, methoxy, ethoxy, butoxy or cyclohexoxy groups or where two of the R' groups may be linked to form a bidentate ligand such as bis(1,2-diphenylphosphine) ethane. The preferred ligand material is selected from triphenylphosphine, tri($C_1$-$C_4$) alkylphosphites and triphenylphosphites. The amount of such phosphorus containing ligand can be for example from 20:1 to 1:10 and preferably from 5:1 to 1:5 moles per gram atom of palladium in the pi-allyl palladium complex.

The solvent in which the reaction takes place can be for example an amide such as dimethylacetamide, dimethylformamide, hexamethylphosphoramide, N-methylpyrrolidone or an unreactive amine such as pyridine. Other suitable solvents include dimethyl sulfoxide and phenylacetonitrile.

The reaction can be conducted at any temperature up to the decomposition temperature of the pi-allyl complex and in general temperatures of up to 200° C. can be used with most complexes. Preferably, however, the reaction is performed at a temperature of from 50° to 175° C. The reaction can be performed at either above or below atmospheric pressure. It is found that pressures up to 30 kg/cm² can be used without seriously jeopardizing the reaction.

Where the reactant is ammonia the products obtained include mono-allylamine, diallylamine and triallylamine. It is found that the proportion of allylamine in the final product can be increased by recycling di- and triallylamine so as to displace the equilibrium reaction mixture in favor of the mono-derivative.

SPECIFIC EMBODIMENTS

The invention is more particularly described by reference to the following Examples. In each case an allyl palladium halide is reacted with ammonia to produce a mixture of allylamines.

EXAMPLE I

This Example describes the effect of a copper salt on the formation of triallylamine by the process of the invention.

Allyl palladium chloride was placed in a reaction vessel provided with means for heating and for the introduction of gases.

15 Ml of dimethylacetamide were then introduced into the reaction vessel which was then pressurized to a pressure of between 6.7 and 9.5 kg/cm² of ammonia at the reaction temperature. The reaction was conducted at the temperature indicated for an hour after which the contents of the reaction vessel were analyzed. The results are indicated below in Table I:

| Moles $CuX_2$ | Moles $C_3H_5PdX$ | Relative Amounts $(C_3H_5)_3N$* | Temp. ° C. |
|---|---|---|---|
| 0 | 0.004 $C_3H_5PdCl$ | 1 | 100 |
| 0.008 $CuCl_2$ | 0.002 $C_3H_5PdCl$ | 71 | 100 |
| 0.008 $CuBr_2$ | 0.004 $C_3H_5PdBr$ | 78 | 100 |

*This column is a measure of the amount of the triallylamine formed in the reaction and hence a measure of the completeness of the reaction. The figure quoted is the height of a chromatogram registering the amount of the triallylamine.

The information presented in the table shows that the addition of cupric chloride or cupric bromide greatly increases the amount of triallylamine registered by the chromatograph and by inference since the tri-allylamine is formed along with diallylamine and monoallylamine, the total amount of allylamine produced.

A similar reaction but of course without the presence of cupric chloride gives a yield of only 28% of triallylamine under comparable conditions.

EXAMPLE II

Ammonia (200 Millimoles) was added at 25° C. to a solution of 3.66g (20 millimoles) of pi-allyl palladium chloride and 2.69g (20 millimoles) of cupric chloride in 80 ml of pyridine contained in an autoclave. The mixture was heated at 100° C for 1¼ hours. A total yield of 61% of allylamines was obtained and of this 7 millimoles (35% of the total) was monoallylamine.

EXAMPLE III

Example II was repeated with the solvent changed from pyridine to a mixture of N-methylpyrrolidone (45ml) and benzonitrile (35 ml). The total yield of allylamines was 47%.

EXAMPLE IV

Example III was repeated with the difference that the amount of $CuCl_2$ was increased to 40 millimoles. The total yield of allylamines was 75%.

EXAMPLE V

A flask was charged with 0.92g (5 millimoles) of $C_3H_5PdCl_2$, 1.49g (11 millimoles) $CuCl_2$ and 11 ml of N-methylpyrrolidone and 9 ml of benzonitrile. After stirring 20 minutes at room temperature, 6.5 ml (75 millimoles) of morpholine were added. In ten minutes the yield of allylmorpholene was 87%.

EXAMPLES VI TO X

The following Examples show the effect various solvents, all run under similar conditions. An autoclave was charged with 20 millimoles of $C_3H_5PdCl_2$, 40 millimoles cupric chloride and 80 ml of solvent. After charging with ammonia the autoclave was brought to 100° and samples at intervals. "Time zero" is taken to be the time when the autoclave reaches 100° C. and is in fact several minutes after the reactants were first mixed.

| Example | solvent | $NH_3$ pressure kg/cu$_2$ | Yield of total allylamines Time Zero | One Hour |
|---|---|---|---|---|
| VI | N-methylpyrrolidone | 10.6 | 27% | 77% |
| VII | dimethylsulfoxide | 11.5 | 20% | 89% |
| VIII | hexamethylphosphoramide | 10.9 | 4% | 69% |
| IX | phenylacetontrile | 8.08 | 23% | 49% |
| X | dimethylacetamide | 10.8 | 17% | 67% |

EXAMPLES XI TO XXIV

The following Examples show the effect of the addition of ligands to the system. The autoclave was charged with 20 millimoles of $C_3H_5PdCl_2$, 20 millimoles of the ligand, 40 millimoles cupric chloride and 80 ml N-methylpyrrolidone. After charging with $NH_3$ the reactor was heated to 100°. Sampling was done as in Examples VI to X.

| Example | Ligand | $NH_3$ pressure kg/cm$_2$ | Yield of total allylamines Time | One Hoar |
|---|---|---|---|---|
| I | none | 10.6 | 27% | 77% |
| XII | triphenylphosphine | 11.4 | 95% | same |
| XIII | triphenylphsophine oxide | 10.6 | 10% | 78% |
| XIV | DIPHOS* | 11.25 | 76% | 68% |
| XV | tributylphosphite | 10.6 | 100% | same |
| XVI | tributylphosphate 10.9 | 14% | 80% | |
| XVII | triphenylphosphite | 9.5 | 83% | 89% |
| XVIII | triphenylphosphate | 10.8 | 10% | 76% |
| XIX | tributylphosphine oxide | 11.4 | 13% | 78% |
| XX | triphenylarsine | 10.8 | 66% | 55% |

The remaining ligands were used at a level only 1/10 the above (i.e. 2 millimoles)

| | | | | |
|---|---|---|---|---|
| XXI | triphenylbismarsine | 10.7 | 46% | 71% |
| XXII | triphenylbismuthene | 10.3 | 41% | 53% |
| XXIII | triphenylstibine | 10.9 | 74% | 71% |
| XXIV | tributoxystibene | 10.4 | 34% | 80% |

* bis (1,2-diphenylphosphine) ethane

EXAMPLE XXV

A run similar to Example II was made with the temperature at 76° C. After 4 hours the yield of allylamines was 21%. A similar run made at 164° C. for 20 minutes gave a yield of 64%. These results indicate that the reaction is enhanced by elevated temperatures.

What we claim is:

1. A process for the production of allylic amines which comprises reacting a pi-allyl palladium complex with a stoichiometric excess of ammonia or an amine having a reactive hydrogen attached to the nitrogen atom and a cupric salt, the reaction taking place at a temperature below the decomposition temperature of the complex and in solution in a solvent for the pi-allyl palladium complex.

2. A process according to claim 1 in which the cupric salt is selected from cupric chloride and cupric bromide.

3. A process according to claim 1 in which the pi-allyl palladium complex is reacted with the cupric salt and an excess of ammonia or amine beyond that required to complex the cupric salt as well as to meet the stoichiometric requirements of the reaction.

4. A process according to claim 1 in which the pi-allyl palladium complex is reacted with a cupric salt and ammonia.

5. A process according to claim 1 in which the reaction temperature is between 50° and 175° C.

6. A process according to claim 1 in which the pi-allyl palladium complex is pi-allyl palladium chloride or pi-allyl palladium bromide.

7. A process according to claim 1 in which a ligand material capable of stabilizing palladium in solution is present during the reaction.

8. A process for the production of allylic amines which comprises reacting a pi-allyl palladium complex having the empirical formula $C_3H_5PdX$ with a cupric salt having the formula $CuX_2$ where in each formula X is Cl or Br, and a stoichiometric excess of ammonia at a temperature of from 50 to 175° C. in the presence of a ligand material having the formula $R'_3M$, wherein M is phosphorus, arsenic, antimony or bisumth and the three R' groups are the same or different hydrocarbyl or hydrocarbyloxy groups.

9. A process according to claim 8 in which the amount of ligand material is sufficient to provide a ratio of from 20:1 to 1:10 moles of ligand per gram atom of palladium in the pi-allyl palladium complex.

10. A process according to claim 8 in which the ligand is selected from triphenylphosphine, triphenylphosphite and tri($C_1$-$C_4$) alkylphosphites.

11. A process according to claim 8 that is performed in a solvent selected from dimethylacetamide, pyridine, N-methylpyrrolidone and dimethylsulfoxide.

12. A process for the production of allylic amines which comprises reacting a pi-allyl palladium complex having the empirical formula $C_3H_5PdX$ with a cupric salt having the formula $CuX_2$ where, in each formula X is Cl or Br, and an excess of ammonia beyond that required to meet the stoichiometric requirements of the reaction and to complex the copper and in the presence of a ligand material selected from triphenylphosphine, triphenylphosphite and tri($C_1$-$C_4$) alkylphosphites in an amount sufficient to provide a ratio of from 5:1 to 1:5 moles of ligand per gram atom of palladium in the pi-allyl palladium complex, the reacton being performed at a temperature of from 50° to 175° C and in solution in dimethylsulfoxide or N-methylpyrrolidone.

* * * * *